United States Patent
Cesarini et al.

(10) Patent No.: US 10,870,826 B2
(45) Date of Patent: Dec. 22, 2020

(54) MODULAR INCUBATOR

(71) Applicant: Comecer S.p.A., Castel Bolognese (IT)

(72) Inventors: Massimiliano Cesarini, Castel Bolognese (IT); Filippo Galassi, Castel Bolognese (IT); Alessia Zanelli, Faenza (IT)

(73) Assignee: Comecer S.p.A.

( * ) Notice: Subject to any disclaimer, the term of this patent is extended or adjusted under 35 U.S.C. 154(b) by 758 days.

(21) Appl. No.: 15/135,986

(22) Filed: Apr. 22, 2016

(65) Prior Publication Data

US 2017/0022468 A1   Jan. 26, 2017

(30) Foreign Application Priority Data

Apr. 23, 2015   (IT) .............................. BO2015A0206

(51) Int. Cl.
*C12M 1/00* (2006.01)
*C12M 1/36* (2006.01)
*C12M 3/00* (2006.01)

(52) U.S. Cl.
CPC ............ *C12M 41/14* (2013.01); *C12M 23/40* (2013.01); *C12M 23/44* (2013.01); *C12M 41/48* (2013.01)

(58) Field of Classification Search
CPC .......... B01L 7/00; B01L 9/00; B01L 2300/04; B01L 2300/18; B01L 2300/0848;
(Continued)

(56) References Cited

U.S. PATENT DOCUMENTS

2005/0244306 A1   11/2005   Stahl
2006/0194193 A1*  8/2006   Tsuruta ................. C12M 29/10
                                               435/4
(Continued)

FOREIGN PATENT DOCUMENTS

CN   202543190 U  * 11/2012 ............ C12M 21/16
DE   202013010260 U   4/2014
(Continued)

OTHER PUBLICATIONS

Takayuki Emura, "English language machine translation". (Year: 2006).*
(Continued)

*Primary Examiner* — Liban M Hassan
(74) *Attorney, Agent, or Firm* — Davidson Berquist Jackson & Gowdey LLP

(57) ABSTRACT

A modular incubator comprising a housing structure divided into cells and having several incubator modules, each of which can be housed, in a removable manner, in a relative cell and is provided with an incubation chamber to incubate microbiological or cellular cultures. Each cell has a first group of connectors and each incubator module has a second group of connectors, each of which can be coupled to a corresponding connector of the first group of connectors of the relative cell when the incubator module is housed in the cell. The first group of connectors has at least one pneumatic connector communicating with at least one source of aeriform substance, and the second group of connectors has a corresponding pneumatic connector communicating with the relative incubation chamber to allow the aeriform substance to be introduced into the incubation chamber.

14 Claims, 4 Drawing Sheets

(58) Field of Classification Search
CPC ........... B01L 2300/0609; C12M 23/04; C12M 23/14; C12M 23/40; C12M 23/44; C12M 23/48; C12M 23/50; C12M 41/14; C12M 41/36; C12M 41/48
USPC ................. 435/4, 286.1, 289.1, 325, 373
See application file for complete search history.

(56) References Cited

U.S. PATENT DOCUMENTS

| | | |
|---|---|---|
| 2010/0316446 A1 | 12/2010 | Runyon |
| 2013/0005014 A1* | 1/2013 | Bell .................. C12N 1/20 435/168 |
| 2013/0102772 A1* | 4/2013 | Eshima ................ G21G 1/10 536/28.2 |

FOREIGN PATENT DOCUMENTS

| | | | | | |
|---|---|---|---|---|---|
| GB | 2237816 A | * | 5/1991 | ............... | B01L 1/02 |
| JP | 2006149232 A | * | 6/2006 | ............ | C12M 23/04 |
| WO | WO2014086984 | | 6/2014 | | |
| WO | WO2014106526 | | 7/2014 | | |

OTHER PUBLICATIONS

Xian et al., "English language machine translation". (Year: 2012).*
Takayuki Emura "English human translation of JP 2006-149232". (Year: 2006).*
Italian Search report—dated Dec. 10, 2015 in ITBO20150206.

* cited by examiner

MODULAR INCUBATOR

The present invention concerns a modular incubator for microbiological and cellular cultures.

BACKGROUND OF THE INVENTION

The known incubators used in biology normally comprise a chamber defined inside a metal supporting box, externally insulated and provided with an adjustable heater to maintain the chamber at optimal temperature. The incubator is provided with autonomous means for controlling, in addition to the temperature, other ambient conditions inside the chamber, for example the percentage of carbon dioxide and the percentage of humidity.

The known incubators cannot be used for simultaneously incubating cultures to be used in very different environments, for example cell regeneration, fertility treatment and transplants, since the cultures in these areas may require very different incubation conditions. The incubator must therefore be used for different cultures at different times or have several incubators for simultaneous use, with consequent increase in the purchasing and management costs for said equipment.

SUMMARY OF THE INVENTION

The object of the present invention is to produce an incubator which is free from the drawbacks described above and, at the same time, is easy and inexpensive to produce.

According to the present invention, a modular incubator is provided as defined in the attached claims.

BRIEF DESCRIPTION OF THE DRAWINGS

The present invention will now be described with reference to the accompanying drawings, which illustrate a non-limiting embodiment example, in which.

DETAILED DESCRIPTION OF THE INVENTION

Figure 1:
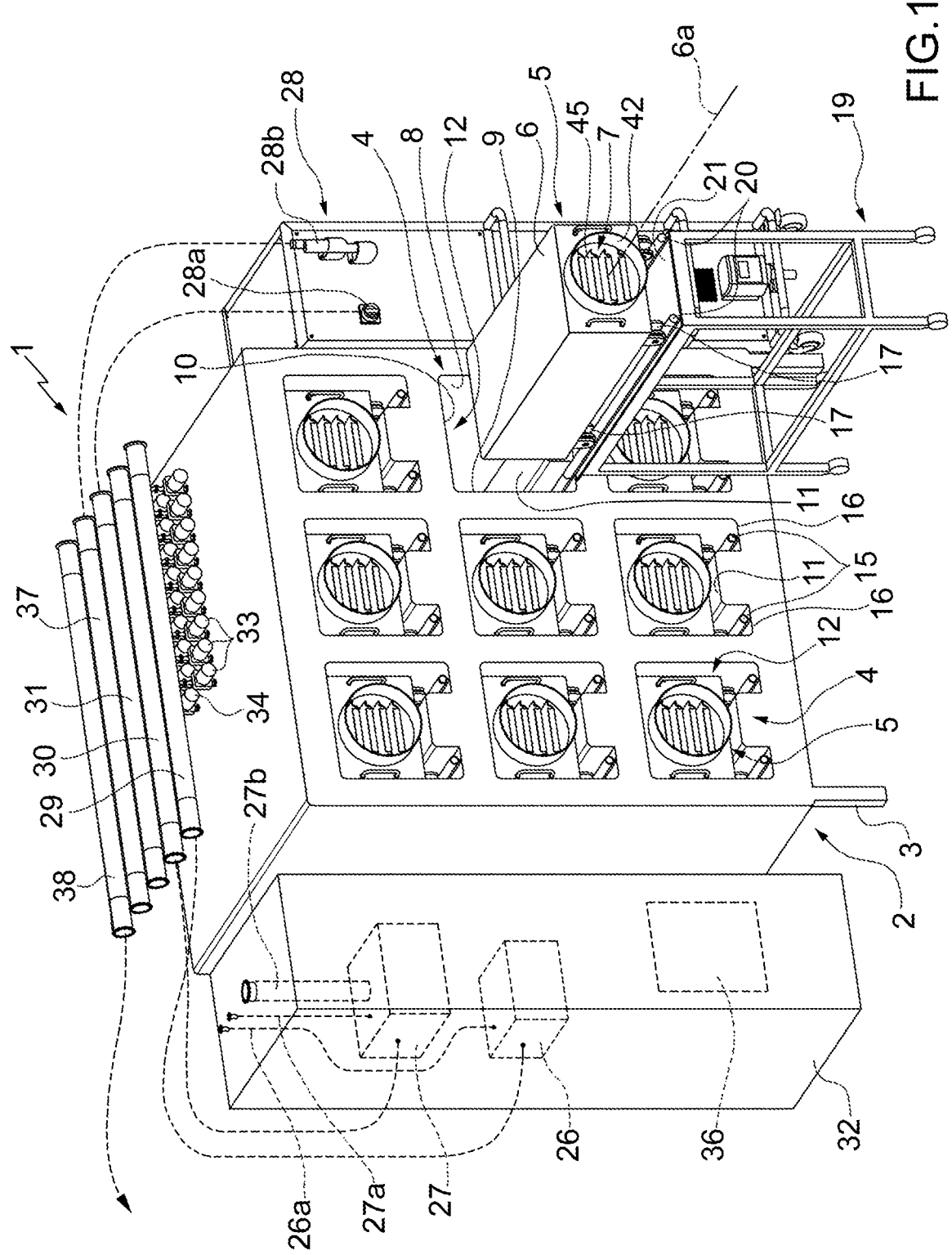
FIG. 1 illustrates the modular incubator of the present invention according to a front three-quarter view.
Figure 2:
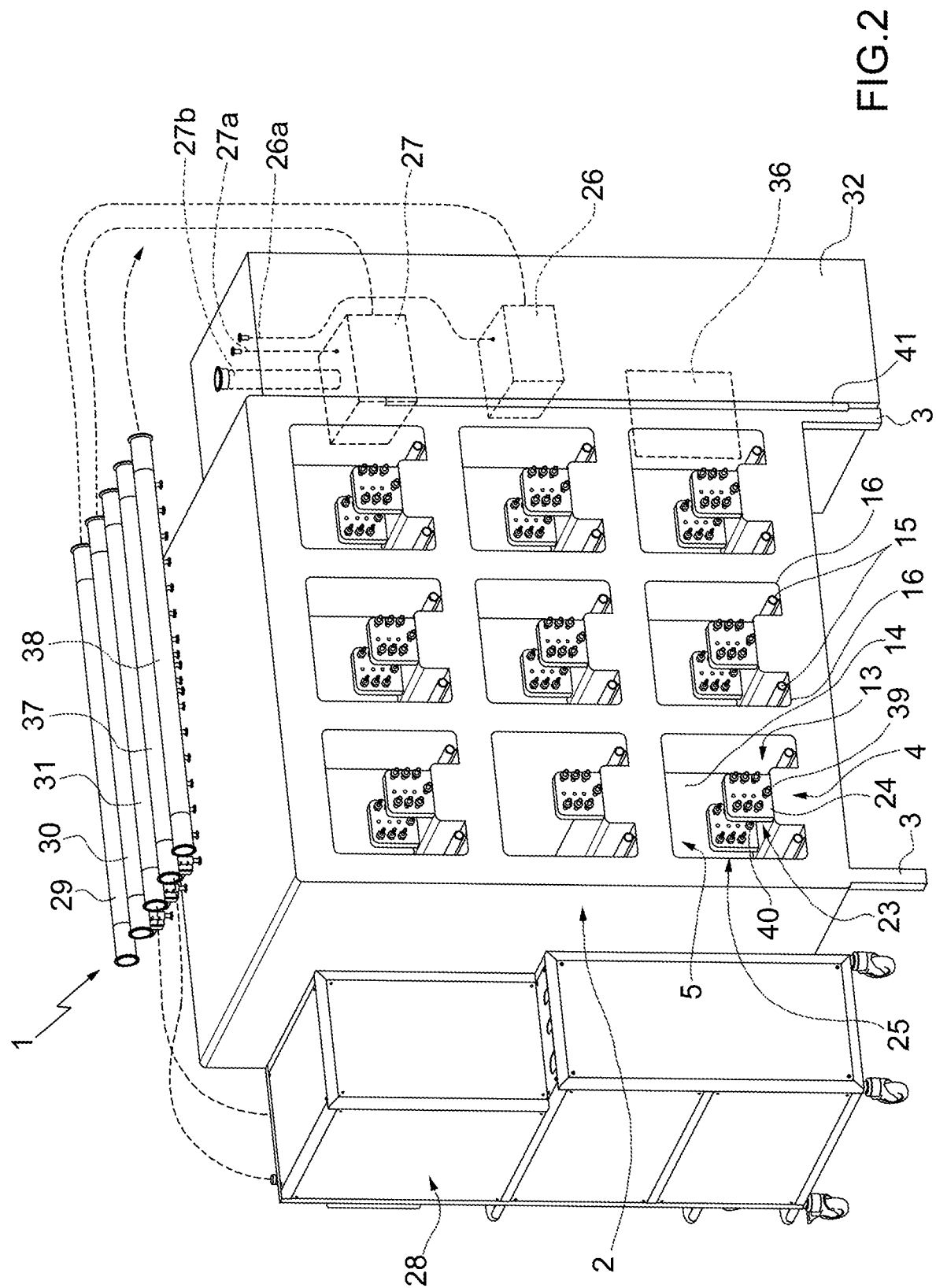
FIG. 2 illustrates the modular incubator of FIG. 1 according to a rear three-quarter view.

In FIGS. 1 and 2, the number 1 generically indicates, as a whole, the modular incubator of the invention. The modular incubator 1 comprises a housing structure 2, which is provided with supporting feet 3 and comprises a plurality of identical cells 4 arranged in several rows according to a regular array, and a plurality of identical incubator modules 5, each of which can be housed, in a removable manner, in a relative cell 4, and comprises a respective outer box 6 which encloses a respective incubation chamber 7 to incubate microbiological or cellular cultures. In the example of the FIGS. 1 and 2, the housing structure 2 comprises nine cells 4 arranged in three rows, and nine incubator modules 5, eight of which are housed in the same number of cells 4 and one outside the remaining cell 4, but ready to be inserted therein. The outer box 6, like the inner walls of the incubation chamber 7, are made of stainless steel.

The outer box 6 of each incubator module 5 has a parallelepipedal shape adapted to be arranged, in use, with an own longitudinal axis 6a in a horizontal direction and having a rectangular cross section. Each cell 4 consists of a channel having a rectangular cross section and a length such as to completely contain the outer box 6. In particular, the cell 4 is defined by two vertical walls, i.e. two lateral walls 8 and 9, and two horizontal walls, i.e. an upper wall 10 and a lower wall 11. The cell 4 has a frontal opening 12 (FIG. 1) for the insertion of an incubator module 5 and a rear opening 13 (FIG. 2), from which a rear wall 14 of the outer box 6 of an incubator module 5 is partially visible when it is housed in said cell 4.

Figure 3:
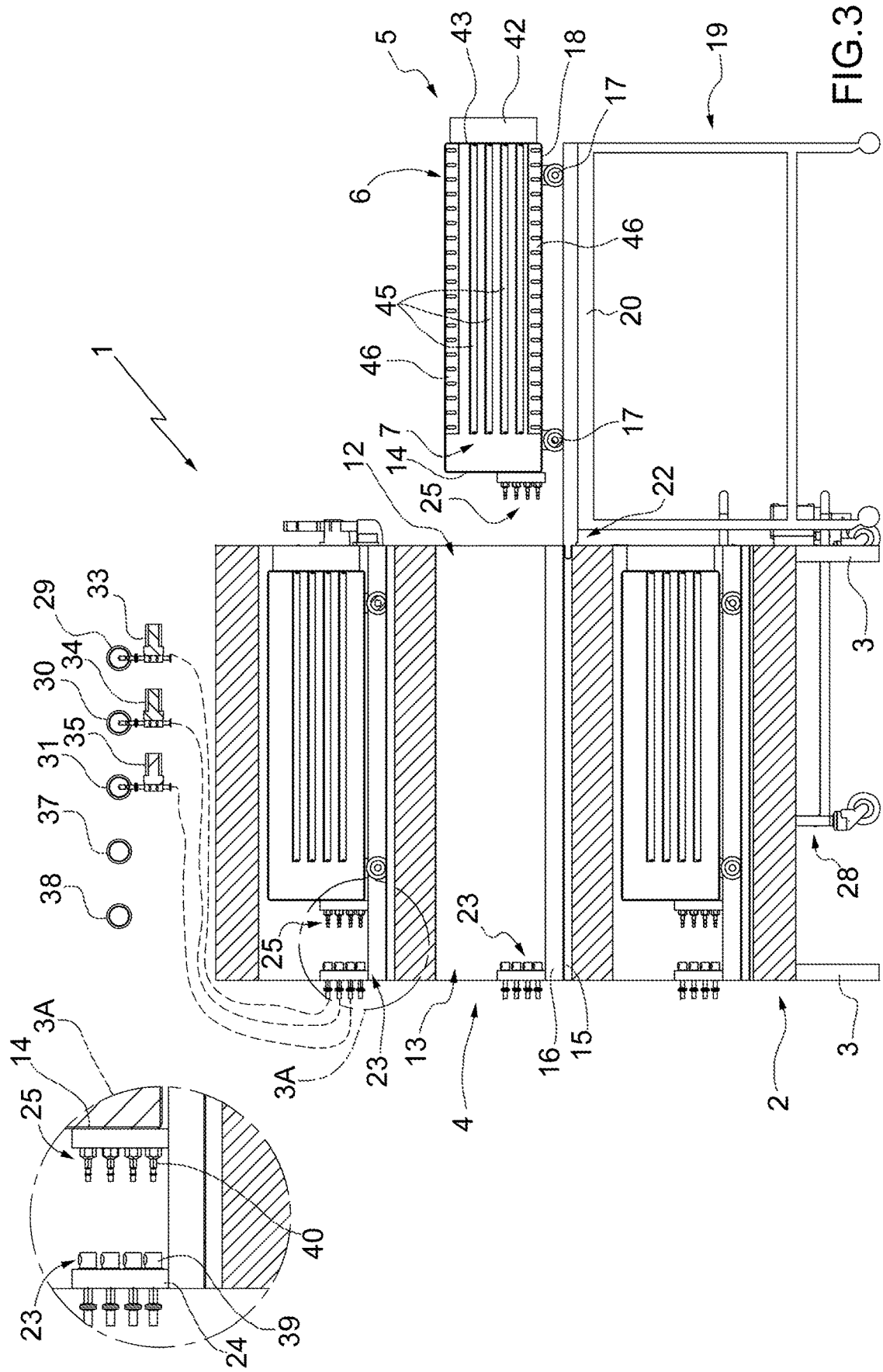
FIG. 3 illustrates the modular incubator of FIG. 1 according to a section view along a plane perpendicular to the frontal plane.

With reference also to FIG. 3, which illustrates the modular incubator 1 according to a section view along a vertical plane passing through the longitudinal axis of the incubator module 5 outside the relative cell 4, each cell 4 comprises a track 15 arranged along a respective pair of grooves 16 positioned at the sides of the lower wall 11 and each incubator module 5 comprises two pairs of wheels 17, which are mounted below a lower wall 18 of the outer box 6 and are adapted to couple in a sliding manner with the track 15 to facilitate insertion and removal of the incubator module 5 into and from the cell 4.

To facilitate the coupling between the wheels 17 and the track 15 during insertion of the incubator module 5 into the cell 4, a trolley 19 is provided having a respective track 20 with the same gauge as the track 15 and fixed on a surface 21 of the trolley 19 which is height-adjustable in order to align the track 20 with the track 15. In FIG. 1, the surface 21 is shown fixed for the sake of simplicity. In FIG. 1, the only incubator module 5 outside the relative cell 4 is shown with the wheels 17 resting on the track 20 of the trolley 19, with the track 20 aligned with and coupled to the track 15 of said cell 4.

The track 20 of the trolley 19 can be coupled to the track 15 of the cell 4 by means of a male-female coupling 22, which can be seen in FIG. 3.

With reference to FIGS. 2 and 3, each cell 4 comprises a respective group of connectors 23 fixed on a vertical plate 24 in turn fixed to the housing structure 2 in the area of the rear opening 13 and each incubator module 5 comprises a respective group of connectors 25 fixed on the rear wall 14 of the outer box 6, each connector of the group 25 can be coupled to a respective connector of the group 23, when the incubator module 5 is housed, or fully inserted, in a relative cell 4. To better show the connectors 25, FIG. 2 illustrates the incubator modules 5 far from the plate 24 and therefore with the connectors 25 decoupled from the respective connectors 23.

The coupling between connectors 23 and connectors 25 is of known type, for example male-female with quick connection-disconnection. For example, with reference to the detail 3A of FIG. 3, the connectors 23 are of female type and the connectors 25 are of male type.

Each group of connectors 23, 25 comprises a respective sub-group of pneumatic connectors and a respective sub-group of electrical connectors. Each pneumatic connector of the group of connectors 25 (on the incubator module 5 side) can be coupled to a respective pneumatic connector of the group of connectors 23 (on the cell 4 side). The pneumatic connectors of the group of connectors 25 communicate with the relative incubation chamber 7. Analogously, each electrical connector of the group of connectors 25 can be coupled to a respective electrical connector of the group of connectors 23. In this way, the coupling between the group of connectors 23 and the group of connectors 25 provides a multiple connection with several airtight channels and several electrical channels.

Each pneumatic connector of the group of connectors 23 of each cell 4 and the corresponding pneumatic connector of the group of connectors 25 of each incubator module 5 are associated with a relative aeriform substance to be introduced into the incubation chamber 7 of the incubator module 5 to carry out the incubation process, or associated with a relative aeriform substance or mixture of aeriform substances to be expelled from the incubation chamber 7 to allow a sterilization cycle before the incubation process or, respectively, to adjust the incubation process.

With reference to FIGS. 1 to 3, three pneumatic connectors of the group of connectors 23 of each cell 4 communicate with relative three sources 26, 27 and 28 of aeriform substances through respective delivery manifolds 29, 30 and 31. Therefore, when the connectors 23 are coupled to the corresponding connectors 25, the aeriform substances can be introduced into the incubation chamber 7.

In particular, the source 26 consists of a delivery device for delivering carbon dioxide, which is housed inside a cabinet 32 of the modular incubator 1 positioned outside the housing structure 2 and is fed by an external circuit, not illustrated, by means of a relative feed duct 26a. The source 27 consists of a water vapour generator which is also housed in the cabinet 32 and supplied with demineralized water and air through respective feed ducts 27a and 27b to provide a flow of humidified air. The source 28 consists of a hydrogen peroxide steam generator, which is enclosed in a respective cabinet mounted on a trolley, illustrated in FIGS. 1 and 2 beside the housing structure 2, and comprises an outlet 28a connected to the respective delivery manifold 31.

Each of the above-mentioned three pneumatic connectors of the group of connectors 23 is connected to the relative delivery manifold 29, 30, 31 by means of a respective valve 33, 34, 35 (FIG. 3) adapted to regulate the flow of the relative aeriform substance towards the relative incubator module 5. Therefore, the number of valves 33, 34, 35 associated with each delivery manifold 29, 30, 31 is equal to the number of cells 4, as can be seen from FIG. 1. The valves 33-35 are electrically or pneumatically controlled by an electronic control panel 36 (FIG. 1) positioned in the cabinet 32.

A pneumatic connector of the group of connectors 23 of each cell 4 communicates with an inlet 28b of the hydrogen peroxide steam generator 28 through a return duct 37 to define, together with the delivery duct 31, a closed circuit used for sterilization of the relative incubation chamber 7. Another pneumatic connector of the group of connectors 23 of each cell communicates with an exhaust manifold 38 to expel the humidified air from the relative incubation chamber 7 and therefore promote a circulation of humidified air enriched with carbon dioxide inside the incubation chamber 7. Said circulation of air inside each incubation chamber 7 is regulated by the relative valves 33 and 34.

The delivery manifolds 29-31, all the valves 33-35 and the return manifolds 37 and 38 are part of the modular incubator 1 and, as shown in the example of FIGS. 2 and 3, they are arranged above the housing structure 2 and preferably covered by an outer casing (not illustrated).

The connections between pneumatic connectors of the group of connectors 23 and the manifolds 29-31, 37, 38 and between the manifolds 29-31, 37 and the sources 26-28 are provided by rigid or flexible pipes, only some of which are illustrated in FIGS. 1-3 by broken lines for the sake of simplicity.

Again with reference to FIGS. 2 and 3, the group of connectors 23 of each cell 4 comprises a particular hydraulic connector 39 which can be coupled to a respective hydraulic connector 40 of the group of connectors 25 of each incubator module 5, in order to drain condensation liquids originating in the relative incubation chamber 7 during the incubation process. The modular incubator 1 comprises a drainage manifold 41 (FIG. 2), which communicates with the hydraulic connectors 39 of all the cells 4 to collect and drain to the outside the condensation liquids and is arranged, for example, along a rear edge of the housing structure 2.

Each incubator module 5 comprises a plurality of sensors (not illustrated) arranged in the relative incubation chamber 7 to monitor the incubation process and the sterilization cycle inside the incubation chamber 7. In particular, said sensors comprise a first sensor for measuring the percentage of humidity, a second sensor for measuring the percentage of carbon dioxide, a third sensor for measuring the concentration of hydrogen peroxide and a fourth sensor for measuring the temperature. Each incubator module 5 further comprises electric heating resistances (not illustrated) to heat the walls of the incubation chamber 7.

The electrical connectors of the first group of connectors 23 of each cell 4 are connected to the control panel 36, while the corresponding electrical connectors of the group of connectors 25 of each incubator module 5 are connected to the relative sensors and to the electrical resistances. Therefore, when the connectors 23 are coupled to the connectors 25, the control panel 36 is able to electrically power the sensors and the electrical heating resistances and receive signals transmitted by said sensors.

The control panel 36 is configured to control the electrical heating resistances and the valves 33-35 as a function of the signals transmitted by the sensors so as to maintain the desired ambient conditions in the incubation chamber 7, said ambient conditions being determined substantially by the following parameters: temperature, percentage of humidity and percentage of carbon dioxide for the incubation process; temperature and concentration of hydrogen peroxide vapours for the sterilization cycle. Furthermore, the control panel 36 is designed to allow an operator to program the above-mentioned parameters for each cell 4, and therefore for the relative incubator module 5 inserted in said cell 4. Therefore, the control panel 36 is able to control the electrical heating resistances and the valves 33-35 so as to maintain, in the incubation chamber 7 of each incubator module 5, the respective desired ambient conditions.

It is observed that maintenance of the desired temperature inside an incubation chamber 7 is obtained via two alternative methods:
  exclusively by controlling (on/off) the electrical heating resistances; or
  controlling the electrical heating resistances and at the same time adjusting the temperature of the water vapour emitted by the water vapour source 27.

Figure 4:
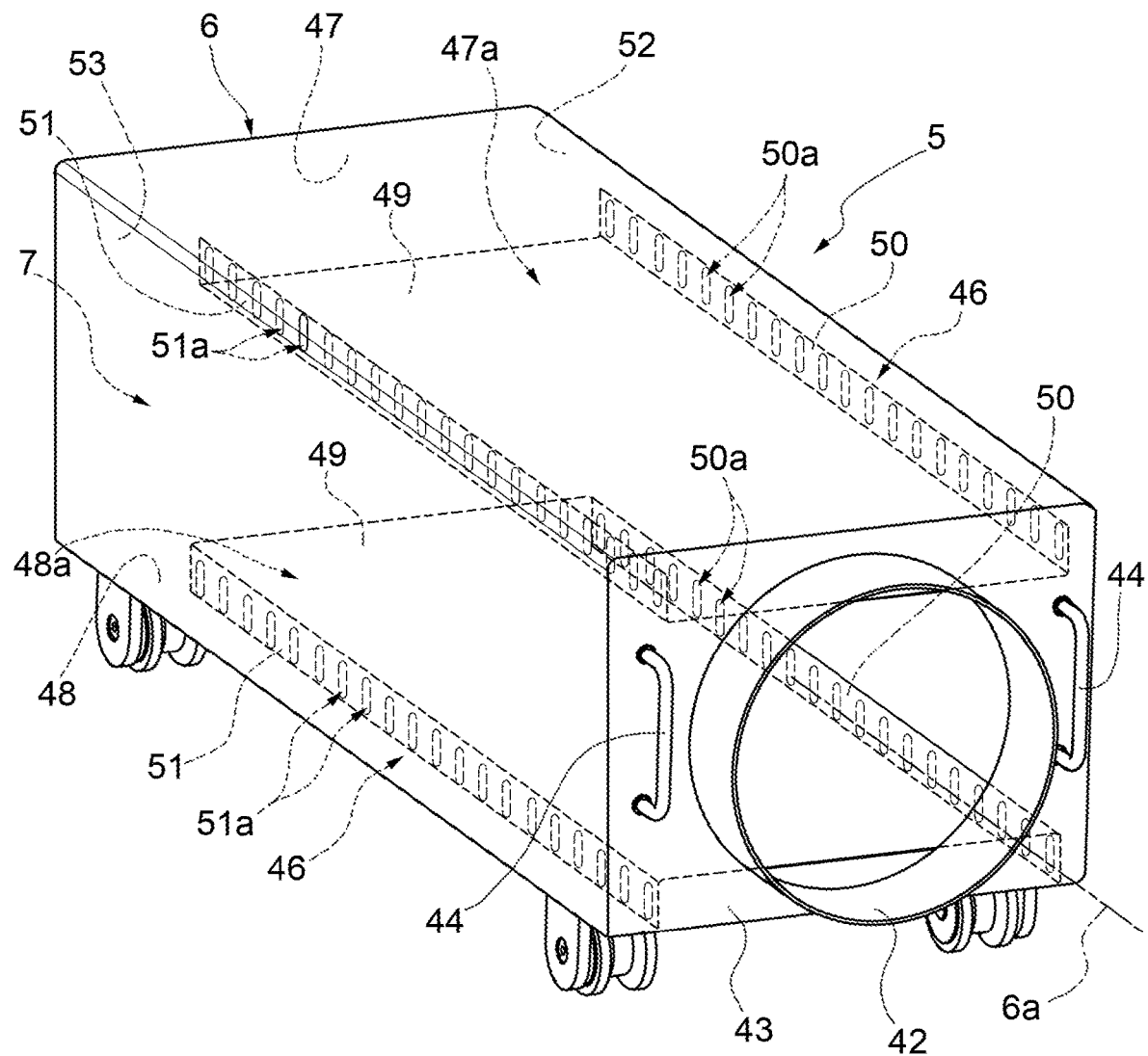
FIG. 4 illustrates details of a module of the modular incubator of FIG. 1.

With particular reference to FIGS. 3 and 4, each incubator module 5 comprises a β-RTP port 42 (Rapid Transfer Port), mounted on a front wall 43 of the outer box 6 and therefore able to couple with a corresponding α-RTP port situated on a wall of an isolator of known type and not illustrated. The coupling between α-RTP and β-RTP ports allows transfer of the content of a relative incubator module 5 into an isolator without jeopardizing the sterility of the contents. Each incubator module 5 further comprises a pair of handles 44 fixed on the front wall 43 on opposite sides of the port 42 to facilitate removal of the incubator module 5 from the relative cell 4.

With reference to FIGS. 1 and 3, each incubator module 5 comprises a plurality of shelves 45 arranged horizontally in the incubation chamber 7, on which it is possible to place the containers with the samples of microbiological or cellular cultures to be incubated. In FIG. 1 the shelves 45 can be seen through a transparent window of the port 42.

With reference again to FIGS. 3 and 4, each incubator module 5 further comprises two diffuser devices 46, which communicate with the pneumatic connectors of the group of connectors 25 which introduce the aeriform substances into the incubation chamber 7 and are arranged inside the latter so as to uniformly distribute the aeriform substances and maintain the temperature uniform in the incubation chamber 7.

With particular reference to FIG. 4, each diffuser device 46 consists of an element with C-shaped cross section, which is fixed on the ceiling 47 or on the floor 48 of the incubation chamber 7 with an own central portion 49 parallel to the ceiling 47 or to the floor 48 so as to define a respective hollow space 47a, 48a extending over the greatest part of the ceiling 47 or floor 48, and which has two lateral portions 50 and 51 provided with respective rows of slits 50a and 51a which establish communication between the hollow space 47a, 48a and the rest of the incubation chamber 7. The slits 50a, 51a of each of the two lateral portions 50 and 51 of each diffuser device 46 are aligned parallel to the longitudinal axis 6a, in the vicinity of a respective lateral wall 52, 53 of the incubation chamber 7. The two lateral portions 50 and are the two portions which define, together with the central portion 49, the C shape of the diffuser device 46 and are transverse, and in particular perpendicular, to the ceiling 47 or floor 48.

Although the invention described above refers in particular to a precise embodiment example, it should not be considered limited to said embodiment example, since it comprises all variations, modifications or simplifications that would be evident to a person skilled in the art, such as:
- a different shape of the box 6 and therefore of the cell 4;
- a housing structure 2 having a different number of cells 4 and/or a different arrangement of the cells 4, with respect to the attached figures;
- cells 4 not identical to one another, in terms of dimensions, and therefore respective incubator modules 5 not identical to one another;
- a number of incubator modules 5, and therefore an even number of cells 4, customisable;
- a different arrangement of the delivery manifolds 29-31 and of the drainage manifold 41 with respect to the housing structure 2;
- one single diffuser device 46 inside the incubation chamber 7;
- each of the two diffuser devices 46 is fixed to a respective lateral wall 52, 53 of the incubation chamber 7;
- the diffuser devices 46 are shorter and arranged with the relative rows of slits aligned parallel to a transverse axis of the outer box 6;
- the incubator modules 5 are without electrical heating resistances and the temperature of the relative incubation chambers 7 is controlled solely by adjusting the temperature of the water vapour generated by the water vapour generator 27; and
- the use of a sole source of aeriform substance for the incubation process, for example the source of carbon dioxide 26, or the water vapour generator 27, for carrying out less refined incubation processes, or the use of further sources of aeriform substances in addition to the sources 26 and 27 for carrying out more refined incubation processes.

One of the main advantages of the modular incubator 1 described above is that it can carry out several incubation processes simultaneously in a corresponding number of incubator modules 5 characterized also by different parameters, such as temperature, percentage of humidity, percentage of carbon dioxide and concentration of hydrogen peroxide vapours, efficiently using common sources of aeriform substances, such as water vapour and carbon dioxide. Furthermore, the modular incubator 1 allows several sterilization cycles to be carried out simultaneously in a corresponding number of incubator modules 5 efficiently using a common source of hydrogen peroxide vapours. Lastly, the incubator module 5, once removed from the modular incubator 1, can be connected to an isolator, by means of the coupling between the β-RTP port 42 and the a-RTP port of the isolator, to allow access to the contents of the incubation chamber 7 without interrupting the sterility inside it.

The invention claimed is:

1. A modular incubator comprising a housing structure having a plurality of cells each of which removably hold one of a plurality of incubator modules, each of the plurality of incubator modules including an incubation chamber to incubate microbiological or cellular cultures; each of the plurality of cells including first connectors and each of the plurality of incubator modules including second connectors, each of which can be coupled to a corresponding connector of the first connectors when one of the plurality of incubator modules is housed in one of said plurality of cells; the first connectors including at least one pneumatic connector in communication with at least one source of an aeriform substance, and the second connectors including a corresponding pneumatic connector communicating with one of the plurality of incubation chambers to introduce the aeriform substance into selected ones of the plurality of incubation chambers; and
further including additional first connectors in the form of additional pneumatic connectors and additional second connectors in the form of additional pneumatic connectors collectively configured to provide a path through which humidified air is exhausted and a supply of humidified air enriched with carbon dioxide is added into selected ones of the plurality of incubation chambers,
wherein each of the plurality of incubator modules includes a diffuser, which communicates with said at least one pneumatic connector and is arranged on the inside of each one of the plurality of incubation chambers so as to uniformly distribute said aeriform substance therein, and
wherein said diffuser comprises at least one elongated element having a C-shaped cross-section, formed from a main wall from which a pair of depending sidewalls depend from opposing side edges, which is fixed on a first wall of said each one of the plurality of incubation chambers to define an inner hollow space extending over a selected length of the first wall wherein each of the depending side walls include a row of slits, which establish a communication between the hollow space and a remaining portion of said each one of the plurality of incubation chambers.

2. The modular incubator according to claim 1 further including an electronic controller; each of the plurality of incubator modules comprising at least one sensor to monitor an incubation process in one of the plurality of incubation chambers; said second connectors comprising at least one electric connector, which is connected to said at least one sensor, and said first connectors comprising a corresponding electric connector, which is connected to the electronic controller so as to transmit signals from said at least one sensor to said electronic controller.

3. The modular incubator according to claim 2, wherein said at least one sensor is located within each of the plurality of incubation chambers and comprises one or more sensors selected within a group comprising a first sensor for measuring humidity, a second sensor for measuring carbon dioxide, and a third sensor for measuring temperature.

4. The modular incubator according to claim 1 and comprising at least one delivery manifold, which is suited to establish communication path between said at least one source of aeriform substance and said at least one pneumatic connector of said first connectors.

5. The modular incubator according to claim 4, wherein said at least one pneumatic connector of said first connectors is connected to said at least one delivery manifold by means of an aeriform substance control valve, which is suited to adjust a flow of the aeriform substance towards selected ones of the plurality of incubator modules.

6. The modular incubator according to claim 5, wherein said electronic controller being configured to control the aeriform substance control valve as a function of the signals transmitted by said at least one sensor of each of the plurality of incubator modules, so as to keep, in each of the plurality of incubation chambers, selected concentration of said aeriform substance.

7. The modular incubator according to claim 1, wherein said first connectors include a first drainage connector and said second connectors include a corresponding second drainage connector; the modular incubator further including a drainage manifold communicating with said first drainage connectors of each of the plurality of cells for collecting condensation liquids produced in each of the plurality of incubation chambers.

8. The modular incubator according to claim 1, wherein said second connectors can be coupled to the corresponding ones of said first connectors by a quick connect-disconnect coupling.

9. The modular incubator according to claim 1, wherein each of the plurality of cells comprises a track and each of the plurality of incubator modules comprises at least one pair of wheels, which are movably coupled to the track so as to make it easier for the plurality of incubator modules to be introduced into and removed from each of the plurality of cells.

10. The modular incubator according to claim 1, wherein each of the plurality of cells comprises a front opening for insertion of one of the plurality of incubator modules, and a rear portion, where said first connectors are fixed; each one of the plurality of incubator modules comprising an outer box having a rear wall, where said second connectors are fixed in positions that allow them to be coupled to the corresponding first connectors, when said one of the plurality of incubator modules is completely inserted into one of the plurality of cells.

11. The modular incubator according to claim 1, wherein each of the plurality of incubator modules comprises an outer box having a front wall, which is provided with a β-RTP port, which can be coupled to an α-RTP port of an isolator.

12. The modular incubator according to claim 1 further including an electronic controller; each of said plurality of incubator modules comprising an electric heater to heat walls of the incubation chamber; said second connectors comprising at least one electric connector, which is connected to the electric heater, and said first connectors comprising a corresponding electric connector which is connected to the electronic controller so as to supply power to the electric heater.

13. The modular incubator according to claim 2,
wherein each of said plurality of incubator modules comprising an electric heater to heat walls of the incubation chamber; said second connectors comprising at least one electric connector, which is connected to the electric heater, and said first connectors comprising a corresponding electric connector which is connected to the electronic controller so as to supply power to the electric heater, and wherein said at least one sensor comprises a temperature sensor and said electronic controller is configured to control said electric heater as a function of the signals transmitted by the temperature sensor, so as to keep a desired temperature within each of the plurality of incubation chambers.

14. A modular incubator comprising a housing structure having a plurality of cells each of which removably hold one of a plurality of incubator modules, each of the plurality of incubator modules including an incubation chamber to incubate microbiological or cellular cultures; each of the plurality of cells including first connectors and each of the plurality of incubator modules including second connectors which can be coupled to a corresponding connector of the first connectors when one of the plurality of incubator modules is housed in one of said plurality of cells; the first connectors including at least one pneumatic connector placed in communication with at least one source of an aeriform substance, and the second connectors including a corresponding pneumatic connector communicating with one of the plurality of incubation chambers to allow the at least one source of the aeriform substance to be introduced into selected ones of the plurality of incubation chambers;
wherein at least selected ones of the plurality of incubator modules includes a diffuser which communicates with said at least one pneumatic connector and is arranged on the inside of at least selected ones of the plurality of incubation chambers so as to uniformly distribute said aeriform substance therein, said diffuser comprises at least one elongated element having a C-shaped cross-section, formed from a main wall from which a pair of sidewalls extend from opposing side edges, the diffuser being fixed on an interior wall of said at least selected ones of the plurality of incubation chambers to define an inner hollow space extending over a selected length of the interior wall wherein each of the side walls include a row of slits, which establish a communication path between the hollow space and a remaining portion of said at least selected ones of the plurality of incubation chambers.

* * * * *